United States Patent [19]

Dunn

[11] 4,305,403
[45] Dec. 15, 1981

[54] URINE RECEPTOR
[75] Inventor: William J. Dunn, Libertyville, Ill.
[73] Assignee: The Kendall Company, Boston, Mass.
[21] Appl. No.: 139,320
[22] Filed: Apr. 11, 1980
[51] Int. Cl.³ .............................................. A61B 19/00
[52] U.S. Cl. ..................................... 128/762; 73/219; 73/427; 128/767; 128/768; 128/771; 128/274; 251/7
[58] Field of Search .............. 128/762, 767, 768, 771, 128/295, 274, 214 E; 251/7; 73/219, 426, 429, 427

[56] References Cited
U.S. PATENT DOCUMENTS

| | | | |
|---|---|---|---|
| 2,471,623 | 5/1949 | Hubbell | 251/7 X |
| 3,213,882 | 10/1965 | Beatty | 251/7 X |
| 3,262,670 | 7/1966 | Marlett | 251/7 |
| 3,415,276 | 12/1968 | Lind et al. | 251/7 X |
| 3,882,899 | 5/1975 | Ginsberg et al. | 251/7 X |
| 3,984,080 | 10/1976 | Varis et al. | 251/7 X |
| 4,095,589 | 6/1978 | Manschot | 128/771 X |
| 4,181,121 | 1/1980 | Schwoboda et al. | 251/7 X |

*Primary Examiner*—Kyle L. Howell
*Attorney, Agent, or Firm*—Powell L. Sprunger

[57] ABSTRACT

A urine receptor comprising, a receptacle having a chamber to receive urine, and a valve assembly attached to a lower portion of the receptacle. The valve assembly is normally closed, and permits passage of urine through the valve assembly when a valve element of the assembly is pressed.

6 Claims, 8 Drawing Figures

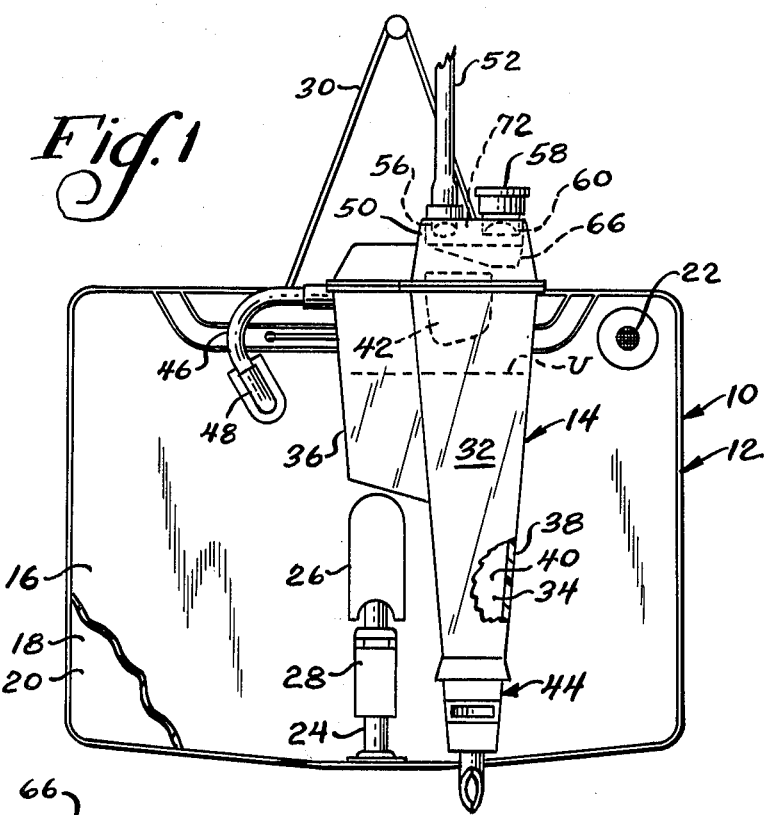
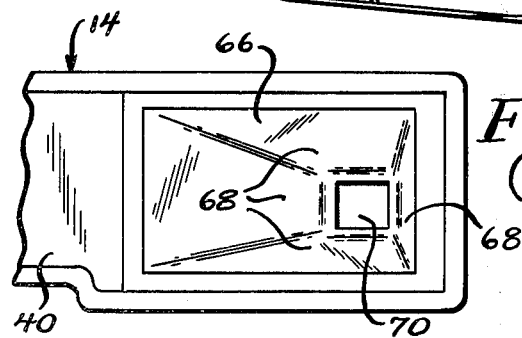
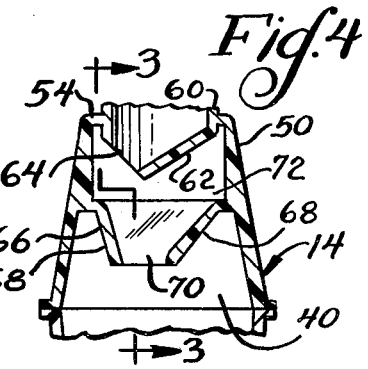
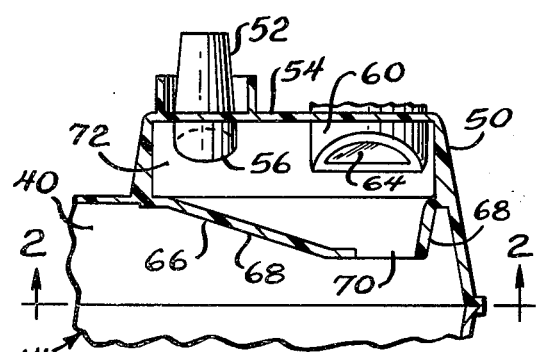
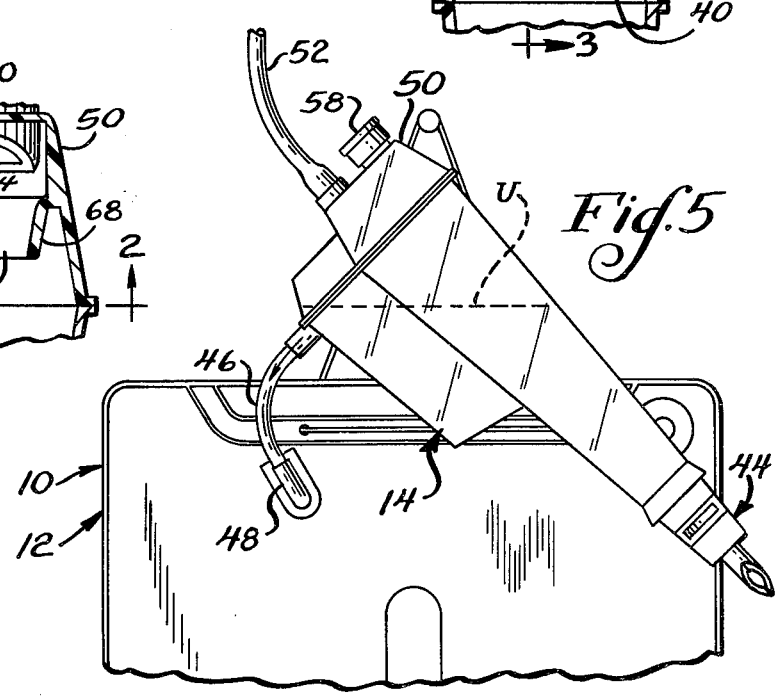

URINE RECEPTOR

BACKGROUND OF THE INVENTION

The present invention relates to urine receptacles.

Before the present invention, a number of urine meters have been proposed for collecting urine from a patient. In general, the urine meters have a container, a receptacle, and a drainage tube communicating with an upper portion of the receptacle. The receptacle may be used to determine incoming urine volumes with relative accuracy, and the receptacle may be periodically emptied into the container where the urine is stored. However, when a urine sample is desired, the sample should be taken from the receptacle where the urine is relatively fresh.

SUMMARY OF THE INVENTION

A principal feature of the present invention is the provision of an improved urine receptor.

The urine receptor of the present invention comprises, a receptacle having a chamber to receive urine. The receptor has means for selectively emptying the receptacle chamber comprising, a valve assembly having a hollow housing attached to a lower portion of the receptacle and having a channel and a front opening communicating with the channel. The valve assembly has an elongated tube of elastic material having one end communicating with the receptacle chamber and extending through the housing channel. The valve assembly has a valve element slidably received in the housing opening, with the valve element having an outer portion located outside the housing, an inner portion defining an aperture extending through the valve element to receive the tube, and a rear portion defining a rear part of the aperture. The valve element is movable between a first position with the rear portion of the valve element spaced from a forward wall portion of the housing, and a second position with the rear portion of the valve element located adjacent an inner part of the forward wall portion. The valve assembly has means for biasing the valve element from the first position to the second position.

A feature of the present invention is that the valve element closes the tube in the second position to prevent passage of urine through the tube.

Another feature of the present invention is that the valve element is normally located in the second position with the tube closed due to the biasing means.

Still another feature of the invention is that the valve element permits the tube to open in the first position to permit passage of urine through the tube.

Yet another feature of the invention is that the valve element may be readily moved to the first position with the tube open by pressing the valve element with one hand outside the housing.

Further features will become more fully apparent in the following description of the embodiments of this invention and from the appended claims.

DESCRIPTION OF THE DRAWINGS

In the drawings:

FIG. 1 is a fragmentary front plan view of a urine meter;

FIG. 2 is a fragmentary lower plan view of a baffle in a receptacle of the urine meter taken substantially as indicated along the line 2—2 of FIG. 3;

FIG. 3 is a fragmentary sectional view taken substantially as indicated along the line 3—3 of FIG. 4;

FIG. 4 is a fragmentary sectional view of a vent and the baffle in the receptacle;

FIG. 5 is a fragmentary front plan view of the urine meter showing the receptacle being tilted to empty urine from the receptacle into a container;

DESCRIPTION OF THE PREFERRED EMBODIMENTS

Figure 6:
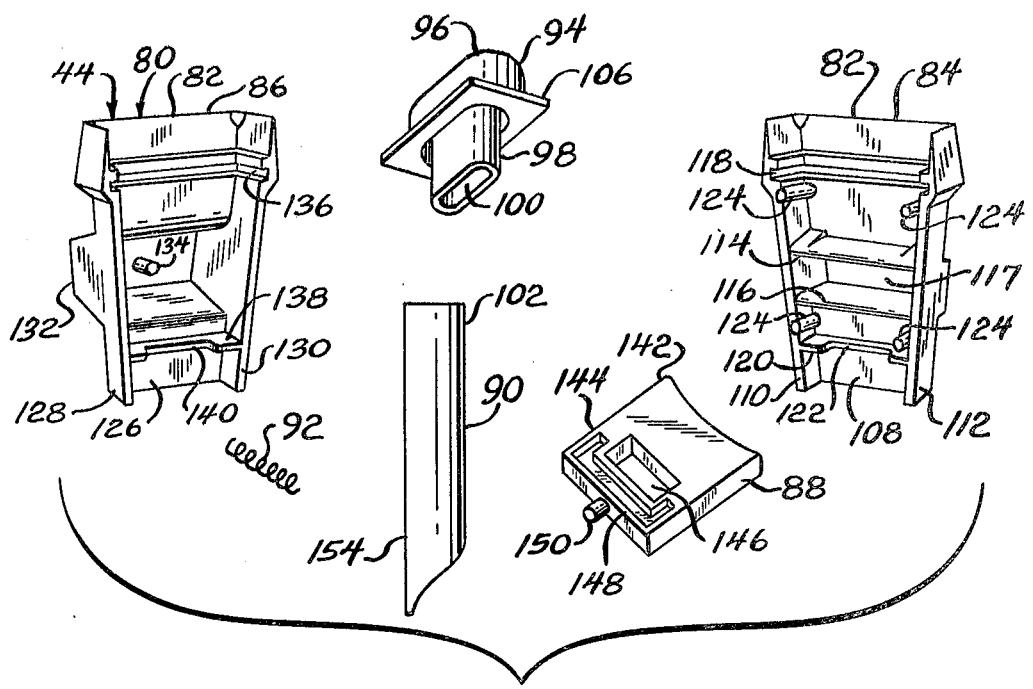
FIG. 6 is an exploded perspective view of a valve assembly for the urine meter receptacle.

Referring now to FIG. 1, there is shown a urine meter generally designated 10 having a container 12 and a receptacle 14. The container 12 has a front wall 16 and a rear wall 18 of flexible material, such as a suitable plastic, being joined together around the periphery thereof and defining a cavity 20 between the front and rear walls 16 and 18. The front wall 16 of the container 12 has a vent 22 with a bacteria filter of known type communicating with the container cavity 20. The container 12 has a tubular section 24 communicating with a lower portion of the cavity 20, and having an outer end removably received in a pocket 26, with the tubular section 24 having a releasable clamp 28 on the tubular section. Thus, when it is desirable to drain urine from the container 12, the tubular section 24 is removed from the pocket 26, and the clamp 28 is released to permit passage of urine through the tubular section 24. The container 12 also has a string 30 attached to an upper portion of the container 12 to permit hanging of the urine meter 10 from a suitable object during use.

With reference to FIGS. 1-4, the receptacle 14 has a front wall 32, a rear wall 34, and a pair of side walls 36 and 38 defining a chamber 40 in the receptacle 14. The receptacle 14 has a hook 42 extending from the rear wall 34 and spaced from the rear wall 34 to receive an upper portion of the container 12 in order to support the receptacle 14 on the upper portion of the container 12. The receptacle 14 has a lower valve 44 to permit draining of urine when desired from the receptacle chamber 40 to obtain a specimen of urine. The urine meter 10 has a flexible tube 46 having one end connected to the receptacle 14 adjacent the side wall 36 such that it communicates with an upper portion of the chamber 40, and the other end of the tube 46 is attached by a connector 48 to an upper portion of the container 12 on the front wall 16, such that the tube 46 communicates with an upper portion of the cavity 20. Thus, the tube 46 communicates between an upper portion of the chamber 40 and an upper portion of the cavity 20 for a purpose which will be described below.

As shown, the receptacle 14 has a raised portion 50 adjacent an upper end of the receptacle 14. The urine meter 10 has a drainage tube 52 for draining urine from the patient, with a downstream end of the drainage tube 52 extending through an upper wall 54 of the raised portion 50 into the receptacle 14 to define a drip tube 56 inside the receptacle 14. The receptacle 14 has a vent 58 attached to the upper wall 54, with the vent 58 having a tubular extension 60 depending inside the receptacle 14. The tubular extension 60 has a generally closed bottom 62, and an opening 64 at one side communicating with the vent 58 which has a bacteria filter element of known type. Thus, the vent 58 permits passage of filtered air from the atmosphere through the tubular extension 60 and opening 64 into the inside of the receptacle 14.

As shown, the receptacle 14 has a baffle 66 extending across the lower part of the raised portion 50, with the baffle 66 having downwardly sloping walls 68 defining a lower opening 70 adjacent the side wall 38. The baffle 66 defines a compartment 72 in the raised portion 50, with the drip tube 56 being located in the compartment 72 above the walls 68 of the baffle 66, and with the tubular extension 60 of the vent 58 being located in the compartment 72 above the baffle opening 70.

In use, urine drains from a catheter (not shown) in the patient through the drainage tube 52 and drip tube 56 into the compartment 72, where it drains along the wall 68 of the baffle 66 through the opening 70 into the receptacle chamber 40. As the urine collects in the chamber 40 of the receptacle 14, the volume of urine may be determined by suitable indicia (not shown) on the front wall 32 of the receptacle 14. When a suitable volume of urine U has been collected in the receptacle chamber 40, as shown in FIG. 1, the urine U may be emptied into the container 12 for retention therein. In order to accomplish this result, the receptacle 14 is lifted from the container 12 to remove the hook 42 from the upper portion of the container 12, and the receptacle 14 is then tilted, as shown in FIG. 5, such that the urine U passes through the tube 46 and the connector 48 into the cavity 20 of the container 12. In this manner, the urine U is transferred from the receptacle 14 to the container 12 in order to initiate collection of a new volume of urine in the receptacle 14. When the receptacle 14 is tilted to pass urine into the container 12, the baffle 66 prevents passage of urine into the drip tube 56 in the event that the receptacle 14 is tilted too far during the emptying procedure. Thus, the baffle 66 eliminates the possibility that urine may reflux into the drip tube 56 and drainage tube 52 in order to minimize the possibility of retrograde bacteria movement into the drainage tube 52 and possibly the patient. Also, the baffle 66 prevents passage of urine into the vent 58 during the emptying procedure in order to prevent closure of the vent 58 which may otherwise be caused by prolonged contact of urine against the filter element of the vent 58. The tubular extension 60 also prevents contact of urine against the vent 58 in the event that urine should splash through the baffle opening 70 when the receptacle 14 is in an upright or tilted configuration.

Figure 7:
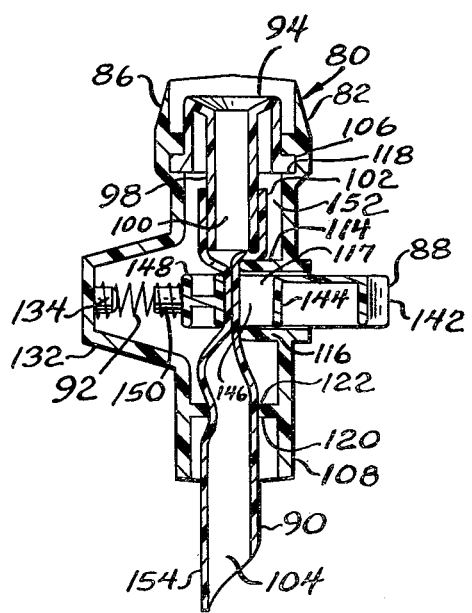
FIG. 7 is a sectional view showing the valve assembly in a closed configuration.
Figure 8:
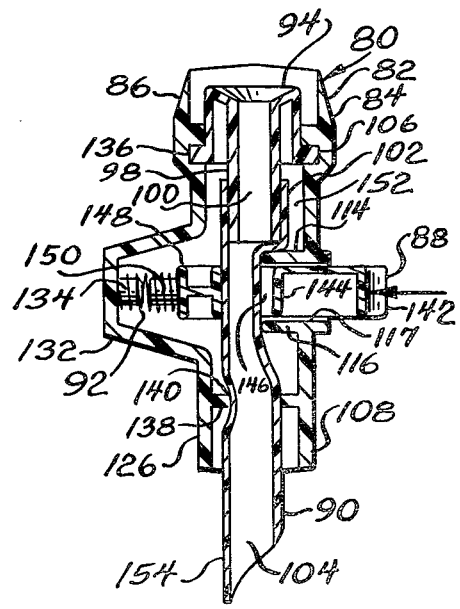
FIG. 8 is a sectional view showing the valve assembly in an open configuration.

With reference to FIGS. 6-8, the valve 44 comprises a valve assembly 80 having a housing 82 with a front housing member 84 and a rear housing member 86, a valve element 88, an elongated tube 90 of elastic material, such as rubber, a helical spring 92, and a retaining member 94. The retaining member 94 has an upper portion 96 and a lower tubular section 98 which is elongated in lateral cross section, with the retaining member 94 having a lumen 100 extending through the tubular section 98. The tubular section 98 is received in an upper portion 102 of the tube 90, with the lumen 100 of the retaining member 94 communicating with a lumen 104 of the tube 90. The retaining member 94 also has an outwardly directed flange 106 extending peripherally around the retaining member 94.

The front housing member 84 has a front wall 108, and a pair of side walls 110 and 112 extending from opposed sides of the front wall 108. The front housing member 84 has a pair of spaced and generally aligned plates 114 and 116 extending inwardly from the front wall 108 and extending between the side walls 110 and 112, such that the plates 114 and 116 define an opening 117 extending between the front and rear of the front housing member 84. The front housing member 84 has a slot 118 in an upper portion of the front wall 108 and side walls 110 and 112. The front housing member 84 also has a lower plate 120 extending inwardly from the front wall 108 between the side walls 110 and 112, with the lower plate 120 having an inner recess 122. The front housing member 84 also has a plurality of pins 124 at spaced locations extending inwardly from inner surfaces of the side walls 110 and 112.

The rear housing member 86 has a rear wall 126, and a pair of side walls 128 and 130 extending from opposed sides of the rear wall 126. As shown, the rear wall 126 has a longitudinal central recessed portion 132 with an inwardly directed pin 134 in a central portion of the recessed portion 132. The rear housing member 86 has a slot 136 in an upper portion of the rear wall 126 and side walls 128 and 130. The rear housing member 86 also has a lower plate 138 extending inwardly from the rear wall 126 between the side walls 128 and 130, with the plate 138 having an inner recess 140.

The valve element 88 has an outer portion 142, and an inner portion 144 defining a rectangular aperture 146 extending through the valve element 88, with a rear portion 148 of the valve element 88 defining a rear part of the aperture 146. As shown, the valve element 88 has a pin 150 extending inwardly from the rear portion 148 of the valve element 88.

The valve assembly is assembled in the following manner. The upper portion 102 of the tube 90 is placed on the tubular extension 98 of the retaining member 94. Next, the tube 90 is passed through the aperture 146 of the valve element 88, and the outer portion 142 of the valve element 88 is passed through the opening 117 until the outer portion 142 is located outside the housing 82. Next, the front housing member 84 is placed against the rear housing member 86 while the spring 92 is connected between the pin 134 on the rear housing member 86 and the pin 150 on the valve element 88. In the assembly configuration, the flange 106 of the retaining member 94 is located in the slot 118 of the front housing member 84 and the slot 136 of the rear housing member 86. Also, the housing 82 in the assembled configuration defines a channel 152 between the front housing member 84 and the rear housing member 86, with the tube 90 extending through the channel 152 and the aperture 146 of the valve element 88, and with the outer portion 142 of the valve element 88 located outside the housing 82. Further, in this configuration the spring 92 extends between the pins 134 and 150, as previously discussed. The housing 82 and retaining member 94 are attached to a lower portion of the urine meter receptacle, with the lumen 100 of the tubular section 98 communicating with the receptacle chamber, such that the lumen 104 of the tube 90 also communicates with the receptacle chamber. As shown, a lower portion of the tube 90 is received between the recesses 122 and 140 of the respective plates 120 and 138 at the lower portion of the housing 82. In a preferred form, the lower end 154 of the tube 90 is located below the housing 82, and may be shaped in a tapered configuration as shown. Also, in the assembled configuration of the housing 82, the pins 124 of the front housing member 84 are received inside the side walls 128 and 130 of the rear housing member 86 in order to stabilize the housing 82 when the front and rear housing members 84 and 86 are attached together. The front and rear housing members 84 and 86 may be permanently connected through use of adhesive along the inner edges of the respective side walls of the front and rear housing members 84 and 86. The front and rear housing members 84 and 86 and the valve element 88 may be constructed from a suitable material, such as plastic.

In the assembled configuration of the valve assembly 80, the valve element 88 is slidably received in the opening 117 of the front housing member 84. With reference to FIG. 8, in a first position of the valve element 88, the rear portion 148 of the valve element 88 is spaced a considerable distance from the inner edges of the plates 114 and 116 in order to enlarge the portion of the aperture 146 located in the channel 152 of the housing 82. Thus, in the first position of the valve element 88, the elastic tube 90 is permitted to expand in the aperture 146 in order to open the tube 90 and permit passage of urine through the tube. With reference to FIG. 7, in a second position of the valve element 88, the rear portion 148 of the valve element 88 is located adjacent the inner edges of the plates 114 and 116, such that the size of the aperture 146 in the channel 152 is substantially reduced. In this configuration, the valve element 88 closes the tube 90 against the inner edges of the plates 114 and 116 in order to prevent passage of urine through the tube 90 in the region of the aperture 146. The spring 92 biases the valve element 88 outwardly from the housing 82, such that the spring 92 biases the valve element 88 from the first open position to the second closed position. Thus, the tube 90 is normally closed, as shown in FIG. 7, with the spring 92 maintaining the valve element 88 in the second position to maintain the valve assembly 80 in the closed position. However, when it is desired to open the valve assembly 80, the outer portion 142 of the valve element 88 is pressed inwardly, as shown in FIG. 8, in order to compress the spring 92, and permit the tube 90 to open. In this manner, the valve assembly 80 may be readily opened through use of one hand to obtain a sample of urine from the receptacle chamber which drains through the tube 90 for collection at the lower end 154 of the tube 90. When a sufficient sample has been obtained, the valve element 88 may be released, and the spring 92 again moves the valve element 88 to its second closed position in order to close the valve assembly 80.

The foregoing detailed description is given for clearness of understanding only, and no unnecessary limitations should be understood therefrom, as modifications will be obvious to those skilled in the art.

I claim:

1. A liquid receptor, comprising:

a receptacle having a chamber to receive body liquids; and means for selectively emptying the receptacle chamber comprising, a valve assembly attached to the receptacle having a hollow housing with a channel and a front opening communicating with the channel, an elongated tube of elastic material having one end communicating with the receptacle chamber and extending through the housing channel, with the other end of the tube being open adjacent the housing and communicating with the atmosphere, a valve element slidably received in the housing opening, said valve element having an outer portion located outside the housing, an inner portion defining an aperture extending through the valve element to receive said tube, and a rear portion adjacent a rear part of the aperture, said valve element being movable between a first position with the rear portion of the valve element spaced from a forward wall portion of the housing such that said tube is open between the valve element rear portion and the housing forward wall portion to permit passage of liquid through the tube, and a second position with the rear portion of the valve element located adjacent an inner part of the forward wall portion to reduce the size of the valve element aperture in the channel and close said tube by squeezing the tube between the valve element rear portion and the housing forward wall portion to prevent passage of liquid through the tube, and means for biasing the valve element from said first position to said second position, the biasing means comprising a helical spring extending between the rear portion of the valve element and a rear wall of the housing.

2. The receptor of claim 1 including a pair of pins extending from the rear wall and rear portion, said pins being received in opposed ends of said spring.

3. The receptor of claim 1 wherein the forward wall portion of the housing comprises a pair of generally aligned spaced plates extending inwardly from a front wall of the housing and defining an inner portion of said opening communicating with the channel.

4. The receptor of claim 1 including a hollow retaining member attached to an upper portion of the housing, said retaining member having a lower tubular section received inside an upper portion of said tube, and said retaining member communicating with the receptacle chamber.

5. The receptor of claim 4 wherein said tubular section is elongated in lateral cross-section.

6. The receptor of claim 1 wherein said housing includes a pair of spaced lower inner plates engaging opposed sides of said tube.

* * * * *